United States Patent [19]

Mandelbaum

[11] 4,221,215

[45] Sep. 9, 1980

[54] ANCHORING AND OCCLUDING SURGICAL DRESSING

[76] Inventor: Isidore Mandelbaum, 803 Springmill La., Indianapolis, Ind. 46260

[21] Appl. No.: 31,371

[22] Filed: Apr. 19, 1979

[51] Int. Cl.³ .......................................... A61F 13/00
[52] U.S. Cl. ................................... 128/155; 128/171; 128/DIG. 26
[58] Field of Search ............................. 128/155–156, 128/165–166.5, 169–171, 275–276, 283, 207.14, DIG. 6, 26, 207.17

[56] References Cited

U.S. PATENT DOCUMENTS

| | | | |
|---|---|---|---|
| 3,286,713 | 11/1966 | Kurtz et al. | 128/156 |
| 3,422,817 | 1/1969 | Mishkin et al. | 128/155 |
| 3,430,300 | 3/1969 | Doan | 128/DIG. 26 |
| 3,682,180 | 8/1972 | McFarlane | 128/DIG. 26 |
| 3,683,911 | 8/1972 | McCormick | 128/DIG. 26 |
| 3,713,448 | 1/1973 | Arrott | 128/207.17 |
| 3,895,629 | 7/1975 | Snyder | 128/171 |

*Primary Examiner*—C. Fred Rosenbaum

[57] ABSTRACT

A surgical dressing used to anchor medical devices, such as chest tubes, to a patient and then to occlude any cut made in a patient for accommodating such medical device includes elongate bands connected to the dressing and to the medical device to connect that medical device to the dressing. The dressing includes a dressing upper portion and a dressing lower portion, and the preferred embodiment of the dressing has adhesive on a rear surface of the dressing upper portion and on the front surface of the dressing lower portion. The dressing upper portion adhesive attaches the dressing to a patient, and after removal of the medical device from a patient, the dressing lower portion is folded over to be superimposed with the upper portion, and is attached to the dressing upper portion via the adhesive on the front surface thereof to occlude the cut made in the patient for accommodating the medical device.

21 Claims, 6 Drawing Figures

ANCHORING AND OCCLUDING SURGICAL DRESSING

BACKGROUND OF THE INVENTION

The present invention relates in general to medical dressings, and, more particularly, to surgical dressings.

After surgery, such as thoracic surgery, or the like, it is often necessary to position a medical device leading into a patient. Such a medical device is, for example, a drainage tube positioned in the thoracic area of a patient. With presently known surgical techniques, such a medical device, and especially a chest tube, is anchored to a patient by suturing a heavy suture to the patient, tieing the suture on the patient, then winding that suture around the medical device.

At the present time, removal of a drainage tube such as a chest tube, or the like, is not only painful for the patient and onerous for the doctor, that removal also carries with it the danger of permitting atmospheric air to enter the thoracic cavity. This danger arises because the thoracic cavity is under negative pressure with respect to the atmosphere. Presently known techniques include steps of inserting a chest tube through an incision made in the patient at the time of surgery or in the emergency room, and then carefully sealing the skin opening, from which the chest tube has its egress from the chest cavity, by gauze or tape. In the usual case, after drainage has stopped via the chest tube, arrangements are made to remove the chest tube while at the same time sealing the opening in the skin so that no air will enter the chest. The present practice includes removing the tape, which has been previously placed at the time of surgery, and any suture between the skin and the chest tube, then quickly removing the chest tube within a few seconds of the removal of the sutures. The skin opening is then occluded with sterile gauze, and while the doctor holds the gauze over the opening, a nurse or other assistant will position several wide strips of adhesive tape over the sterile gauze covering the skin opening to form an occlusive dressing.

There are several drawbacks to the presently used technique. Among these drawbacks are: removal of tape from the skin may be painful; additional gauze sponges are required to be ready to occlude the skin opening; and the assistance of a nurse or resident doctor is usually required to complete the removal procedure.

Accordingly, there is need for a dressing which is complete and readily available from the time surgery is performed and a tube, such as a chest tube, is placed in position until that tube is removed.

There is also a need for a dressing which will minimize the pain and discomfort associated with the removal thereof from the patient. In known devices, additional tape makes such removal a painful experience for the patient.

There is also a need for a dressing which permits removal thereof and occlusion of a skin opening performable by a single, unaided person.

While there are many devices known which anchor medical devices to a patient (see, e.g., U.S. Pat. Nos. 2,606,555, 3,677,250, 3,765,421, 3,834,380, 3,856,020, 3,885,560, 3,826,254, 3,895,629, 3,957,048 and 4,057,066), these devices all have drawbacks because the medical device is not anchored in a manner applicable to tubes, such as drain tubes, or require special dexterity to apply. Furthermore, none of these known devices has any provision for readily occluding a skin opening after removal of the medical device.

Attention is specifically directed to U.S. Pat. Nos. 3,918,446 and 4,122,857, which disclose devices for anchoring articles, such as catheters, to a patient. In both of these devices, the article is sandwiched between a pair of pads which are held together adhesively to hold the article in position on a patient. These devices are not amenable for use with drainage tubes. U.S. Pat. No. 4,122,857, in particular, is not amenable for use with articles wherein the area neighboring the skin opening should be protected as well as having the article securely anchored to the patient.

It is noted that both of the just-mentioned patents are directed to holding small intravenous type devices in place, and neither device has any means for sealing or dressing the skin opening after removal of the medical instrument. These devices therefore have several important drawbacks.

SUMMARY OF THE INVENTION

The surgical dressing embodying the teachings of the present invention anchors a medical device, such as a drain tube, or the like, to a patient and is quickly and easily removed by a single, unaided individual. Once the medical device is removed, the dressing is used as a covering to occlude the skin opening and maintain desired conditions in the area surrounding that opening.

The preferred embodiment of the surgical dressing described herein includes two equal parts. Both parts are attached to each other and therefore appear as a single dressing. The upper half of the dressing includes adhesive on the rear face thereof with an opening defined therethrough. In one embodiment, the opening is circular and is located centrally of the dressing upper part. Antibiotic gauze, or the like, is located in the area neighboring the central opening. The adhesive is used to attach the dressing upper half to a patient. The gauze has an opening defined therethrough for permitting egress of a drainage tube, such as a chest tube. The dressing upper half, in the preferred embodiment, also has two tapes which encircle and are tied to a chest tube to anchor that tube to the chest wall near the site of the tube egress. In the preferred embodiment, the lower half of the dressing is equal in size to the upper half and includes adhesive on the front face thereof. The lower half of the tape has the adhesive surface thereof reversed with respect to the dressing upper half so that the portion which will contact the patient's body is non-adhesive. The adhesive side of the lower half is covered by a paper or plastic wrap which may easily be stripped for exposing the adhesive surface. In one embodiment, the mid-portion of the lower dressing portion includes an inherent antibiotic gauze pledget. This dressing lower portion may be considered to be a skirt; and, simultaneously with removal of the drainage tube from the patient's body, the lower half of the dressing will be sealed over the upper half of the dressing to completely occlude the gauze opening from which the chest tube was removed.

Thus, the dressing of the present invention anchors a medical device such as a chest tube to a patient. In one embodiment, a chest tube emanates from an incision in the human thorax and passes through a gauze which is impregnated with antibiotic ointment or antibacterial solution. The gauze is adherent to the underside of a rectangular segment of adhesive tape which is adherent to the patient's skin. This adhesive tape is located on either side of the gauze pledget and has cotton tape or similar suture material incorporated therein which permits anchoring of a chest tube to the dressing and therefore to the chest wall.

In the preferred embodiment, the lower portion of the dressing includes an equal sized rectangular adhesive dressing which is covered by a sterile leaflet. An antibiotic impregnated gauze pledget is positioned in the center of this adhesive dressing.

To remove a chest tube, the anchoring tapes or sutures are severed on each side of the gauze pledget. Then, the cover protecting the adhesive on the dressing lower portion is removed to expose the lower half adhesive and gauze. As the attendant removes the chest tube from the thorax with one hand, that same attendant, essentially simultaneously therewith, raises the lower adhesive dressing with his other hand and seals that dressing lower half to the upper dressing half to completely seal the gauze pledget and the opening in the patient's chest wall.

The occlusive chest tube dressing of the present invention permits complete care of the wound and skin opening for the chest tube. The dressing includes means to isolate the skin opening after the tube is removed but nearly simultaneously with such removal to prevent ingress of any air from the atmosphere to the negative pressure thorax and also to prevent bacterial contamination of the skin opening incision. If there is ingress of air following removal of the chest tube, it may lead to collapse of a lung, to severe acute disability, or even to death. The dressing embodying the teachings of the present invention substantially eliminates these possibilities while permitting easy manipulation thereof by a single, unaided individual.

The dressing of the present invention thus securely anchors a device, such as a chest tube, to a patient, yet is easily placed and removed without inducing undue pain for the patient. While the dressing anchors the device to a patient, desired conditions are maintained in the vicinity of the opening by that dressing. Once the medical device is removed, the same dressing occludes the opening in the skin and provides any desired environment for that opening. The dressing can be changed from primarily an anchoring device to primarily a closure device by a single person, and is immediately available for use from the time the medical device is placed on the patient to, and including, the time that medical device is removed from the patient. As one person can perform the just-described operation, much cost and time will be saved as opposed to present procedures which require at least two trained people to remove a medical device, such as a drainage tube.

OBJECTS OF THE INVENTION

It is, therefore, a main object of the present invention to provide a surgical dressing which will both anchor a device to a patient and occlude an incision for that device when the device is removed.

It is another object of the present invention to provide a surgical dressing which minimizes pain and discomfort associated with removal of an anchoring device.

It is yet another object of the present invention to provide a surgical dressing which will both anchor a device to a patient and occlude an incision for that device when the device is removed and which can be operated by a single unaided person.

It is still another object of the present invention to provide a surgical dressing which makes a complete dressing available from the time of surgery wherein a chest tube is placed in a patient until that chest tube is removed.

These together with other objects and advantages which will become subsequently apparent reside in the details of construction and operation as more fully hereinafter described and claimed, reference being had to the accompanying drawings forming part hereof, wherein like reference numerals refer to like parts throughout.

DETAILED DESCRIPTION OF THE INVENTION

Figure 1:
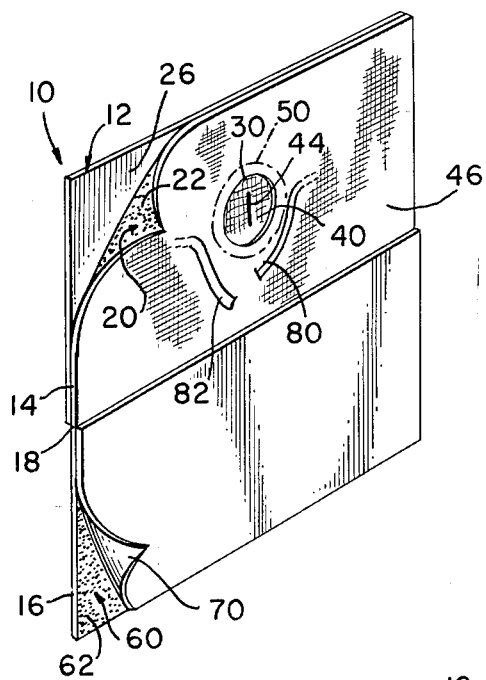
FIG. 1 is a perspective of a surgical dressing embodying the teachings of the present invention.

Shown in FIG. 1 is one form of the surgical dressing embodying the teachings of the present invention. The surgical dressing in FIG. 1 is denoted by the reference indicator 10, and includes a unitary planar body 12 having a dressing upper portion 14 and a dressing lower portion 16. The portions 14 and 16 can be joined along a hinge, a foldline, or a fold area, indicated by the phantom line 18, if so desired. The body is preferably unitary, and divided into two essentially equal portions or halves, but can include a pair of unequally sized juxtaposed portions integrally connected to each other at selected edges thereof by a foldline or hinge, or the like. Furthermore, the preferred peripheral shape of the dressing 10 and the dressing portions 14 and 16 is rectangular or polygonal, however, other shapes, such as arcuate, irregular, or the like, can be used without departing from the teaching of the present invention.

The dressing upper portion 14 is preferably a gauze type material, but can be other materials used in surgical dressings if so desired, or the upper portion 14 can include a combination of such materials with gauze interwoven into another type of material, if suitable.

First attaching means, such as adhesive 20, is located on a rear surface 22 of the dressing upper portion and is used to attach the dressing 10 to a patient. Accordingly, the adhesive 20 is of the type generally employed for effecting such a function, and attaches the dressing to the body or skin of a patient in a manner secure enough to carry out the functions described herein for the dressing 10. Other attaching means can also be used in place of adhesive 20 if suitable, and the adhesive can also include antibiotics if so desired.

A removable protective sheet 26 covers the adhesive 20 and is stripped off prior to application of the dressing to a patient. The protective sheet is sized and dimensioned to essentially completely cover the rear face of the dressing upper portion, and may be of the type used to maintain antiseptic conditions on the dressing protected thereby.

An opening 30 is defined through the dressing upper portion 14, and is shown in FIG. 1 to be arcuate, or circular in shape. However, other shapes can be used, as indicated by the rectangular outline for opening 30' in FIG. 3. Other opening shapes can also be used, and can include star shapes, irregular polygons, or the like. The opening 30 is preferably located centrally of the dressing upper portion 14, but other positions can be used as suitable.

A gauze pledget 40 spans the opening 30, and in the preferred embodiment, is impregnated with antibiotic material. The gauze of the pledget 40 may be the same or a continuation of the gauze forming the dressing upper portion, or may be a different gauze, or may have a greater thickness than the rest of the gauze forming the dressing upper portion. The pledget 40 can include adhesive located around the peripheral edges thereof which will contact the adhesive 20 and thereby securely attach the pledget to the upper portion 14. The type and dimensions for the pledget 40 will be determined according to the desired functions therefor. The gauze of pledget 40 can be interwoven or otherwise integrated into the gauze forming the dressing upper portion 14 if so desired.

Figure 6:
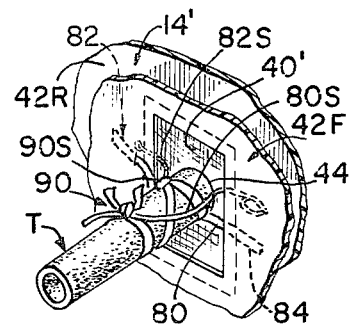
FIG. 6 is a perspective view of another form of the surgical device embodying the teachings of the present invention.

An interleaved pledget is shown in FIG. 6. The pledget 40' is interpositioned and captured between a pair of layers 42R and 42F which are coextensive with each other and which together form the dressing upper portion 14'. The layers 42R and 42F with the pledget 40' entrapped therebetween are facially connected together to form an integral dressing upper portion. In this manner, the front and rear surfaces of the dressing upper portion can be selected from those materials best suited for the chosen application, and the gauze pledget can be selected from those materials and dimensions best suited for the desired application therefor. Thus, for example, the rear layer 42R can be selected from those materials most compatible with a patient's skin or body, while the front layer 42F can be selected for the strength and shielding characteristics thereof.

Figure 3:
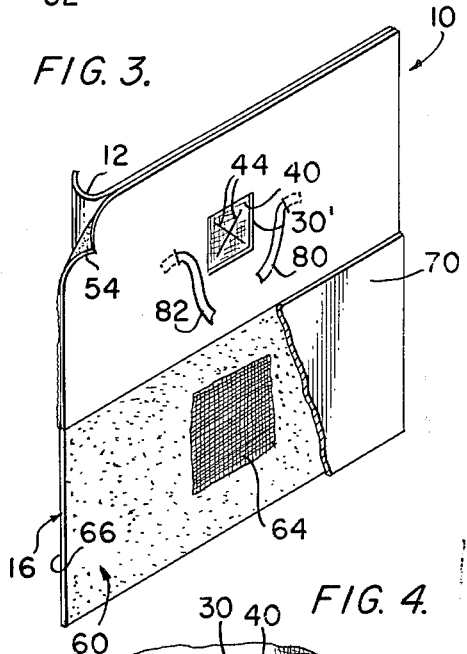
FIG. 3 is a perspective view of another form of a surgical dressing embodying the teachings of the present invention.

A slot 44 is defined in the gauze pledget and can be in the form of a single slot as shown in FIG. 1, or a pair of crossed slots which extend diagonally of an opening as shown in FIG. 3. The slots can be of any suitable length and can extend completely across the opening 30, or only partially thereacross, as suitable. The purpose of the slot 44 will be discussed below.

A front surface 46 of the dressing upper portion 14 is exposed to the environment prior to and during use of the dressing, and thus is subject to contact with bacteria and other means which are potentially harmful to a patient. The front surface is formed of a material which can maintain a sterile field beneath the dressing if suitable. To further protect the patient, the opening 30 can be covered by a removable protective shield 50 indicated by the phantom lines in FIG. 1. The shield 50 will preferably have a peripheral shape corresponding to the shape of the opening 30, and be slightly larger than such opening to cover and thus protect same. The shield 50 and the protective sheet 26 thus maintain antiseptic conditions on the gauze pledget 40 prior to use of the dressing 10. Both elements are removed prior to use of the dressing 10.

The material, or materials, selected for the dressing upper portion 14 will be subject to considerations of strength, availability and use conditions as will be apparent from the discussion presented hereinafter.

The lower dressing portion 16 can be formed of gauze or adhesive tape as suitable, although adhesive tape is preferred because that tape can seal the opening 30 in a secure manner. Second attaching means, such as a layer of adhesive 60, or the like, is located on front surface 62 of the dressing lower portion 16. The adhesive 60 can completely cover the front surface 62, or be located in patches thereon as suitable. Furthermore, the adhesive 60 will not be expected to contact a patient, and accordingly, need not be antibiotic; however, the adhesive 60 can be any type of adhesive suitable to carry out the desired function. Of course, it may be desirable to include antibiotic type adhesive in an area on the lower dressing portion corresponding to the area of opening 30, as will be apparent from the discussion presented below. However, a preferred embodiment of the dressing 10 includes a gauze pledget 64 located centrally of the dressing lower portion 16 as shown in FIG. 3. The gauze pledget 64 is dimensioned to occlude the opening 30 in an antiseptic manner when the pledget 64 is superimposed thereover. As will be described below, the gauze pledget 64 protects the opening 30 when superimposed thereon. The pledget 64 can be adhered to the dressing lower portion or incorporated thereinto, as desired.

The dressing lower portion 16 has a rear surface 66 which will be used to form a protective outer layer for the dressing, as will be discussed below. As such, the dressing lower portion 16 is preferably formed of a material suitable for this purpose. Like the multilayered dressing upper portion shown in FIG. 6, the dressing lower portion can also be formed of a plurality of superimposed, coextensive layers, one of which is used to form the just-mentioned protective outer layer, and another layer being located adjacent opening 30 and receiving adhesive 60 for being adhered to the dressing upper portion.

A removable protective sheet 70, such as a sterile leaflet, or the like, covers the adhesive 60 on the dressing lower portion. In the preferred embodiment, the protective sheet 70 completely covers the dressing lower portion while leaving the dressing upper portion exposed, as shown in FIG. 1. However, a protective shield can cover both portions, and can be either unitary or bipartite with an upper portion thereof removed when the upper portion of the dressing 10 is to be used.

Figure 2:
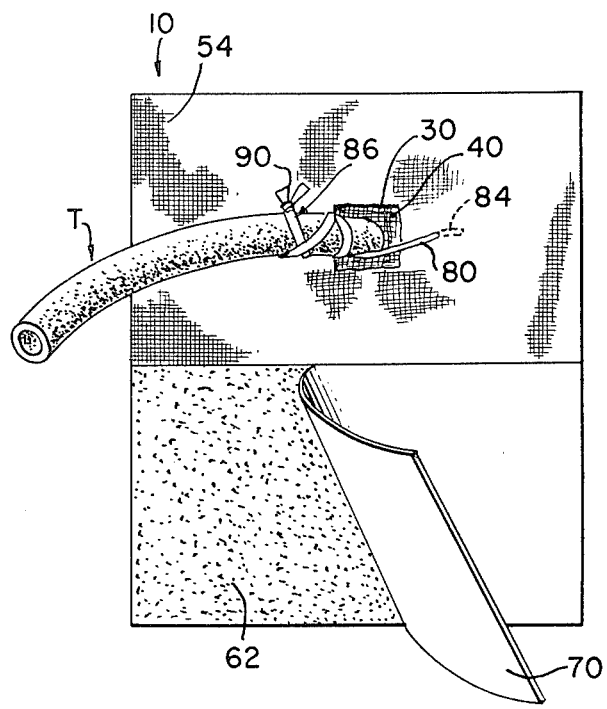
FIG. 2 is a front view of a surgical dressing embodying the teachings of the present invention with a chest tube projecting therefrom.

As best shown in FIGS. 1 and 2, a pair of elongate bands 80 and 82 are mounted on the dressing upper portion. In the preferred embodiment, each band is flexible and, more preferably, is cotton tape, suture material, or like material used in surgical applications. Both bands or straps are identical and accordingly, only strap 80 will be described, it being understood that the description is equally applicable to strap 82. As best shown in FIG. 2, strap 80 has one end 84 thereof securely mounted on the dressing upper portion near the opening 30. The strap end 84 can be attached to the dressing by fusing, welding, interlacing, integrating, interfelting, or the like, of the strap or strap elements into the gauze of either the dressing upper portion 14 or the gauze of the pledget 40. The strap end 84 can also be attached to the gauze by interweaving same with that gauze. This is especially so if the strap is formed of a braidable yarn or gauze material itself. The strap end 84 is shown in FIG. 2 in phantom lines to indicate the secure attachment thereof to the body of the dressing. The strap can be attached to the rear face of the dressing upper portion via the adhesive 20, or in other manners to be described presently. In any event, the attachment of the strap 84 should be secure. The strap can also be entrapped between the layers 42F and 42R in the FIG. 6 embodiment if so desired. An intermounted strap can also be fused to either or both of these layers as suitable.

Figure 4:
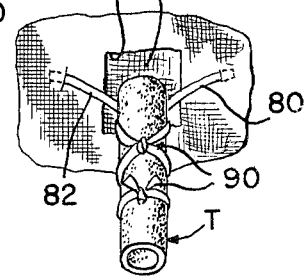
FIG. 4 is a perspective view of chest tube tied in place on a surgical dressing embodying the teachings of the present invention.

The other end 86 of the strap 80 is free and is adapted to be connected, as by tieing or the like, to a surgical device, such as a drainage tube T extending out of the opening 30 at an angle with respect to the dressing 10. As shown in FIGS. 2 and 4, the straps are twisted about the tube T in a multi-convolutant manner and are tied together in a knot 90 to thereby firmly and securely anchor the tube T to the dressing. The straps 80 and 82 are preferably co-equal in length and are long enough to form the knot 90 at a location spaced from the dressing far enough to tether the tube T securely enough to essentially prevent movement of that tube in an axial direction thereof, that is, into or out of the opening 30. The tube T is thus harnessed by the interknotted and intertwisted straps 80 and 82 to be immobilized sufficiently to perform the function desired therefor. If the tube T is used as a thoracic drainage tube, immobility thereof is highly desirable, as is the case for other uses of devices similar to the tube T. As is shown in FIG. 4, the straps can be knotted together at several locations to form a plurality of knots 90 to thereby further ensure secure anchoring or bridling of the tube T. The spacing between the strap ends 84 and the opening 30 is determined according to the position initial contact with the tube T, the stability of the harness, manufacturing considerations, and the like. It is also noted that further strap sections can be spliced or tied to the stap ends 86 to lengthen the straps if the need arises to stabilize a tube which has a strong tendency to move. Furthermore, several straps, in addition to straps 80 and 82, can be used, and located surrounding the opening 30. Thus, the two straps shown and described herein is a preferred form only and is not intended to be a limitation.

As shown in FIG. 6, additional straps 80S and 82S can be used to secure the tube T. The straps 80S and 82S each include a suture stitched to the patient's skin and tied in place to the patient's skin. The straps are then tied to the skin suture and guided through the slot 44 adjacent the tube T. The straps 80S and 82S are then tied to the tube T. The straps 80S and 82S can be intertwisted with the straps 80 and 82, or can be twisted and tied together separately of those straps 80 and 82, see, for example, knot 90S in FIG. 6. The straps 80S and 82S add safety to the anchoring of the tube T because that tube is anchored to both the dressing 10 and to the patient's skin. It is preferable to use the X-shaped arrangement of slot 44 shown in FIG. 3 when using the additional straps 80S and 82S. It is easier to bring the tube T and the skin sutures through the X-shaped slot than through other shapes of that slot.

Figure 5:
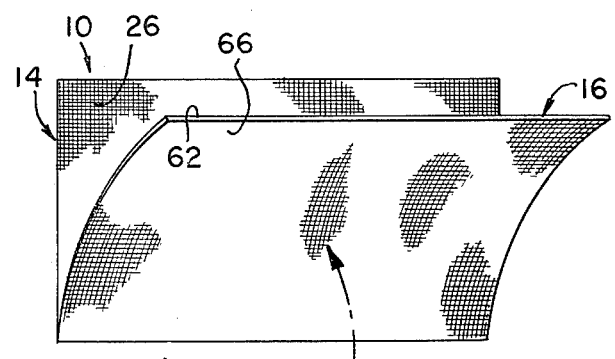
FIG. 5 is a perspective view of a surgical dressing embodying the teachings of the present invention being folded to occlude an opening in a patient after removal of a medical device, such as a chest tube.

Referring to FIGS. 1, 2 and 5, use of the dressing 10 will now be described. After surgery, a tube, such as a chest tube, or the like, may be required for drainage or the like. In the case of the chest tube, the tube emanates from an incision in the human thorax and extends at an angle with respect to the patient's body outwardly thereof.

The protective sheet 26 is removed from the dressing 10 thereby exposing the patient adhering adhesive 20, and the opening 30 is also exposed. The dressing is positioned so the tube T will be received through the slot 44, and then forced over that tube into contact with the patient. The dressing is securely adhered to the patient once properly oriented with respect to the tube T. The gauze pledget 40 is preferably impregnated with antibiotic material so that proper conditions are maintained in the neighborhood of the body opening.

The straps 80 and 82 (and 80S and 82S, when used) are twisted about the tube and tied, or otherwise connected, thereto to anchor that tube in place. The in-place dressing is shown in FIGS. 2, 4 and 6.

The procedure employed during the removal of the tube T is greatly simplified over known procedures due to the dressing 10. To effect this removal, the protective sheet 70 is stripped from the dressing lower portion 16, then the straps 80 and 82 (and 80S and 82S) are severed, as by cutting or the like. The person removing the tube then pulls the tube out with one hand while essentially simultaneously therewith folds the dressing lower portion upwardly as indicated in FIG. 5, by arrow A.

The dressing lower portion is folded upwardly about either a hinge or a foldline, or a fold area, or the like, and is superimposed onto the dressing upper portion. Adhesive 60 adheres to the dressing upper portion front surface to ensure the dressing upper and lower portions together and to thus form a protective dressing covering the opening in which the tube T was accommodated. The protective gauze pledget 64 essentially completely occludes the opening 30 and thus maintains this area in a sterile and antibiotic environment, or in any other environment deemed necessary therefor. The anchoring device is thus transformed into an occlusive dressing for the opening in the patient's body.

One person can thus quickly and easily remove the tube, such as a chest tube, or the like, while minimizing any danger of permitting atmospheric air to enter the patient's body, especially the thoracic cavity wherein a negative pressure exists.

The dressing 10 thus not only serves as an anchoring or holding means for devices such as the tube T, but also serves as a covering for the opening in the patient once the device, such as tube T, is removed. The dual function for the dressing 10 provides great versatility thereto.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:
1. A surgical dressing comprising:
 a dressing upper portion having a rear surface adapted to contact a patient, a front surface adapted to face away from a patient, attaching means on said rear surface for attaching said dressing upper portion to a patient, an opening defined in said dressing upper portion, an elongate band attached at one end thereof to said dressing upper portion adjacent said opening, said band having another end thereof adapted to be attached to a medical device extending through said opening and at an angle with respect to said upper portion, said another end being adapted to be attached to such surgical device at a location spaced from said dressing upper portion front surface for anchoring such medical device to a patient via said dressing upper portion; and a dressing lower portion foldably connected to said dressing upper portion, said dressing lower portion having a rear surface and a front surface, second attaching means on said dressing lower portion front surface which attaches to said dressing upper portion front surface when said dressing lower portion is positioned to overlie said dressing upper portion so that when said lower portion overlies said upper portion those dressing portions are attached together with said dressing lower portion completely convering and occluding said opening area to prevent foreign matter from passing through said opening when no surgical device is located in said opening.

2. The surgical dressing defined in claim 1 further including a second elongate band attached at one end thereof to said upper dressing portion adjacent said opening and having another end thereof adapted to be attached to such medical device and being adapted to be attached to such medical device at a location spaced from said upper portion front surface.

3. The surgical dressing defined in claim 2 wherein said bands are flexible and are tied to the medical device.

4. The surgical dressing defined in claim 1 wherein said opening is circular in shape.

5. The surgical dressing defined in claim 1 wherein said opening is rectangular in shape.

6. The surgical dressing defined in claim 1, 4 or 5 further including a gauze pledget spanning said opening, said gauze pledget having a slot defined therethrough for receiving the medical device.

7. The surgical dressing defined in claim 1 wherein the medical device is a chest drainage tube.

8. The surgical dressing defined in claim 1 or 6 further including a lower dressing portion gauze pledget located on said dressing lower portion to cover said opening when said dressing lower portion is superimposed on said dressing upper portion.

9. The surgical dressing defined in claim 3 wherein said dressing upper portion includes gauze and said band one ends are interwoven into said gauze.

10. The surgical dressing defined in claim 3 further including a gauze pledget spanning said opening, said gauze pledget having a slot defined therethrough for receiving the medical device wherein said band one ends are interwoven into said gauze.

11. The surgical dressing defined in claim 1 further including a removable protective shield over said opening.

12. The surgical dressing defined in claim 1 wherein said first and second attaching means include adhesive.

13. The surgical dressing defined in claim 1 wherein said dressing upper portion includes a plurality of layers.

14. The surgical dressing defined in claim 13 further including a gauze pledget spanning said opening, said gauze pledget having a slot defined therethrough for receiving the medical device.

15. The surgical dressing defined in claim 6 wherein said slot is linear.

16. The surgical dressing defined in claim 15 wherein said slot is X-shaped.

17. The surgical dressing defined in claim 2 further including sutures attached to a patient and second bands attached to said sutures, said second bands being adapted to extend through said opening and being adapted to be attached to the medical device.

18. The surgical dressing defined in claim 8 wherein said gauze pledgets include antibiotic materials.

19. The surgical dressing defined in claim 12 further including removable protective shields on said adhesive.

20. The surgical dressing defined in claim 1 wherein the dressing is unitary.

21. A surgical dressing comprising:

a dressing upper portion having a rear surface adapted to contact a patient, a front surface adapted to face away from a patient, attaching means on said rear surface for attaching said dressing upper portion to a patient, an opening defined in said dressing upper portion, an elongate band attached at one end thereof to said dressing upper portion adjacent said opening, said band having another end thereof adapted to be attached to a medical device extending through said opening, said another end being adapted to be attached to such surgical device at a location spaced from said dressing upper portion front surface for anchoring such medical device to a patient via said dressing upper portion;

a dressing lower portion foldably connected to said dressing upper portion, said dressing lower portion having a rear surface and a front surface; and second attaching means positioned to attach said dressing upper portion front surface to said dressing lower portion front surface when said dressing lower portion is positioned to overlie said dressing upper portion so that when said lower portion overlies said upper portion those dressing portions are attached together with said dressing lower portion completely covering and occluding said opening area to prevent foreign matter from passing through said opening when no surgical device is located in said opening.

* * * * *